United States Patent [19]
Weber

[11] 3,931,211
[45] Jan. 6, 1976

[54] OXAZOLE COMPOUNDS, PROCESS FOR THEIR MANUFACTURE AND USE THEREOF

[75] Inventor: Kurt Weber, Basel, Switzerland
[73] Assignee: Ciba-Geigy AG, Basel, Switzerland
[22] Filed: Sept. 6, 1973
[21] Appl. No.: 394,940

[30] Foreign Application Priority Data
Sept. 15, 1972 Switzerland.................. 13547/72

[52] U.S. Cl.... 260/307 D; 252/301.2 W; 260/468.5; 260/514.5; 260/544 M; 260/559 A; 260/571; 260/575
[51] Int. Cl.²........................................ C07D 263/56
[58] Field of Search................................ 260/307 D

[56] References Cited
UNITED STATES PATENTS
3,586,673   6/1971   Bloom et al. ................. 260/240

Primary Examiner—Raymond V. Rush
Attorney, Agent, or Firm—Joseph G. Kolodny; Edward McC. Roberts; Prabodh I. Almaula

[57] ABSTRACT

The present invention provides new oxazole compounds of the formula

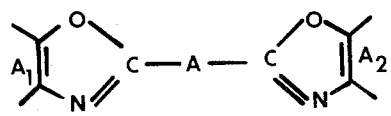

wherein A represents a 9,10-dihydrophenanthrene radical which is bonded in 2,7-position to the oxazole radicals and which can contain lower alkyl or alkoxy groups or halogen atoms as substituents, $A_1$ and $A_2$ each independently represents an optionally non-chromophorically substituted benzene or naphthalene radical which is condensed in the customary manner with the oxazole ring.

The new compounds are valuable optical brighteners for organic materials, especially polyesters.

5 Claims, No Drawings

OXAZOLE COMPOUNDS, PROCESS FOR THEIR MANUFACTURE AND USE THEREOF

The present invention relates to new oxazole compounds, a process for the manufacture of these compounds, and to their use as optical brighteners for organic materials.

The new oxazole compounds according to the present invention are the compounds of the formula (1) 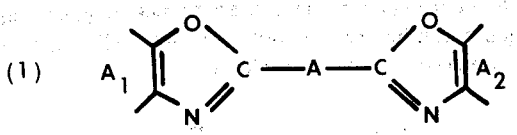

wherein A represents a 9,10-dihydrophenanthrene radical which is bonded in 2,7-position to the oxazole radicals and which can contain lower alkyl or alkoxy groups or halogen atoms as substituents, $A_1$ and $A_2$ each independently represents an optionally non-chromophorically substituted benzene or naphthalene radical which is condensed in the customary manner with the oxazole ring.

The non-chromophoric substituents of the benzene and naphthalene radicals in $A_1$ and $A_2$ can be both monovalent and divalent radicals, these latter forming a carbocyclic or heterocyclic ring which is fused to the benzene or naphthalene ring.

Compounds within the scope of formula (1) are, for example, those of the formula (2) 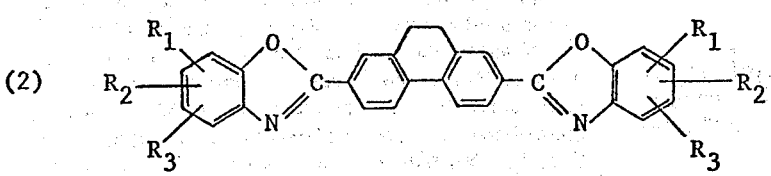

wherein $R_1$ represents hydrogen, halogen, alkyl with 1 to 18 carbon atoms and containing as substituents cyano, carboxy, carbalkoxy with 2 to 9 carbon atoms, carbamoyl, or carbamoyl substituted at the nitrogen with alkyl or hydroxyalkyl, alkoxy with 1 to 18 carbon atoms, phenyl or phenoxy optionally substituted with halogen, alkyl with 1 to 4 carbon atoms or alkoxy with 1 to 4 carbon atoms, alkenyl with 3 or 4 carbon atoms, cyclopentyl, cyclohexyl, phenylalkyl or phenylalkoxy, each with 1 to 4 carbon atoms in the alkyl or alkoxy moiety and optionally substituted in the phenyl moiety with halogen, alkyl with 1 to 4 carbon atoms or alkoxy with 1 to 4 carbon atoms, carboxy, carbalkoxy with 2 to 9 carbon atoms, carbamoyl, carbamoyl substituted at the nitrogen with alkyl or hydroxyalkyl, cyano, alkylsulphonyl or alkyloxysulphonyl with 1 to 12 carbon atoms, phenylsulphonyl or phenoxysulphonyl optionally substituted with halogen, alkyl with 1 to 4 carbon atoms or alkoxy with 1 to 4 carbon atoms, sulphamoyl, sulphamoyl substituted at the nitrogen with alkyl or hydroxyalkyl with 1 to 12 carbon atoms, the sulpho group and salts thereof, $R_2$ represents hydrogen, alkyl with 1 to 18 carbon atoms, alkoxy with 1 to 18 carbon atoms, alkenyl with 3 to 4 carbon atoms, cyano or the sulpho group and salts thereof, or $R_1$ and $R_2$ in ortho-position to each other represent a fused benzene radical, tetramethylene, trimethylene, or methylenedioxy, $R_3$ represents hydrogen, halogen, alkyl with 1 to 4 carbon atoms or alkoxy with 1 to 4 carbon atoms.

To be singled out for particular attention are the compounds of the formula (3) 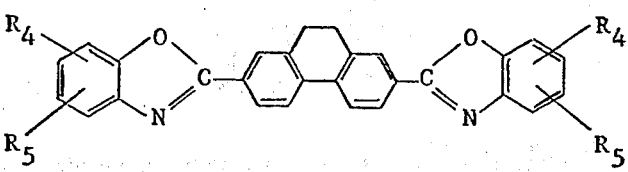

wherein $R_4$ represents alkyl or alkoxy with 1 to 4 carbon atoms, phenyl or phenoxy, $R_5$ represents hydrogen or alkyl with 1 to 4 carbon atoms, and $R_4$ and $R_5$ in ortho-position to each other represent a fused benzene ring, tetramethylene, or trimethylene.

Compounds having particular utilities are those of the formulae (4) 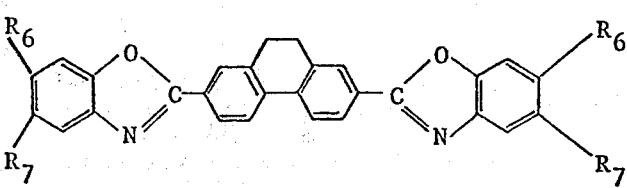

wherein $R_6$ represents alkyl or alkoxy with 1 to 4 carbon atoms, phenyl or phenoxy, and $R_7$ represents hydrogen or alkyl with 1 to 4 carbon atoms, or $R_6$ and $R_7$ together represent tetramethylene or trimethylene, and (5) 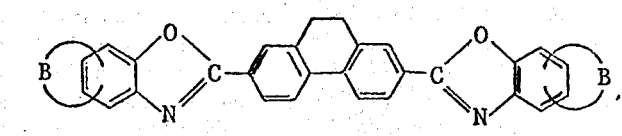

wherein B represents a fused benzene ring. Within the scope of formula (5) the preferred compound is that of the formula

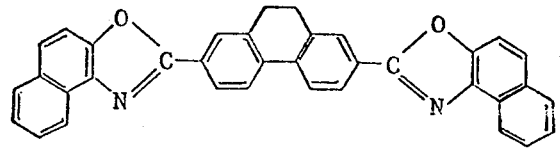

(6)

The compounds of the formula (1) and of the secondary formulae can be manufactured by processes analogous to known ones.

For example, the process of oxazole cyclisation is used, wherein a start is made from the corresponding acylamides. In its general form this method consists in subjecting to cyclisation reaction a compound of the formula (7) 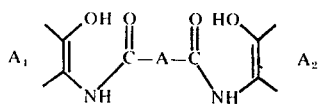

by heating it to temperatures above 100°C, optionally in the presence of a catalyst.

The acyl compounds of the formula (7) required for the process cited hereinabove are manufactured by reacting one mole of a compound of the formula (8) 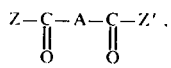

wherein Z and Z' each independently represents hydroxyl, alkoxy with 1 to 4 carbon atoms or halogen, preferably chlorine, with one mole of each of the aminophenols of the formulae (9) 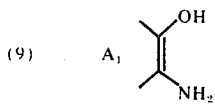 and (10) 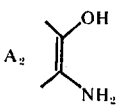

If Z and Z' are identical or are functions of similar reactivity and $A_1$ and $A_2$ are different from each other, there will be obtained a statistical mixture of three different compounds. It is frequently possible to dispense with a separation of these different compounds and of the end products arising therefrom, since the use of such mixtures is often advantageous.

If it is intended to use symmetrical types, then of course one will choose $A_1 = A_2$.

If it is desired to manufacture asymmetrical types it is exedient to choose for Z and Z' functions with clearly differing reactivity, halogen for Z and alkoxy for Z', and reaction is performed successively with one mole of a compound of the formula (9) and one mole of a compound of the formula (10). It is also possible to manufacture asymmetrical types by first effecting in a primary condensation product of the formula

(11) 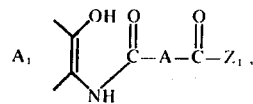

wherein $Z_1$ represents preferably hydroxyl or alkoxy with 1 to 4 carbon atoms, in a manner analogous to that indicated hereinbefore, initially a one-sided cyclisation to the compound of the formula

(12) 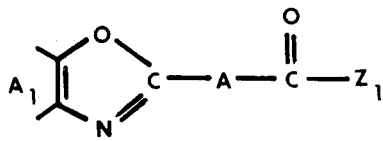

and then repeating the analogous reaction sequence with an aminophenol of the formula (10) at the remaining carboxyl function.

The reaction between the components of the formulae (8), (9) and (10) can take place with or without intermediate separation of the initially resulting intermediate stages of the formula (7) by heating to elevated temperatures, for example to 120° to 130°C, advantageously in an inert gas, e.g. a flow of nitrogen, the reaction optionally being carried out in the presence of a catalyst. Examples of suitable catalysts are: boric acid, boric anhydride, zinc chloride, p-toluenesulphonic acid, also polyphosphoric acids including pyrophosphoric acid. If boric acid is used as catalyst, this is used advantageously in an amount of 0.5% to 5%, based on the total weight of the reaction mass. It is possible to use simultaneously high-boiling polar, organic solvents, for example dimethyl formamide, dichlorobenzene, trichlorobenzene, and aliphatic, optionally etherified oxy compounds, e.g. propylene glycol, ethylene glycol monoethyl ether, diethylene glycol diethyl ether, or diethylene glycol dibutyl ether, or high-boiling esters of phthalic acid, e.g. dibutyl phthalate.

If the process is carried out in two steps, it is possible to condense initially a compound of the formula (8) with an o-amino compound of the formula (9) and (10) in the presence of an inert organic solvent such as toluene, xylene, chlorobenzene, dichlorobenzene, trichlorobenzene, or nitrobenzene, at temperature between 100° and 200°C, and to convert the resulting acyl compounds of the formula (7) at temperatures between 150° and 350°C, optionally in the presence of a catalyst, into the azole compound of the formula (1). If carboxylic acid chlorides are used as starting materials, these can be manufactured immediately before the condensation with the o-amino compound from the free carboxylic acid and thionyl chloride, optionally with the addition of a catalyst, e.g. pyridine, in the solvent in which the condensation afterwards tales place.

A particularly advantageous process for the manufacture of compounds of the formula (2) consists e.g. in subjecting the acyl compounds obtained by condensation of 2 moles of o-aminophenol of the formula

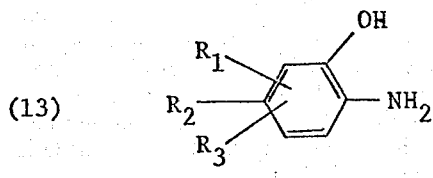

(13)

with 9,10-dihydrophenanthrene-2,7-dicarboxylic acid chloride, without isolation, to an oxazole cyclisation reaction by treatment with a dehydrating agent at temperatures between 120° and 350°C.

Among other possible methods of manufacture there may be mentioned the reaction of a compound of the formula $$NC - A - CN \qquad (14)$$

with o-aminophenols of the formulae (9) and (10) at elevated temperatures, preferably 160° to 260°C. Advantageously this reaction is carried out in the presence of agents which bind ammonia, e.g. phosphoric acid, polyphosphoric acid, or phosphorus pentoxide, in an ert gas.

Another frequently useful process for manufacturing compounds of the formula (1) consists in the condensation of ortho-haloanilines with a compound of the formula (8) in accordance with the scheme

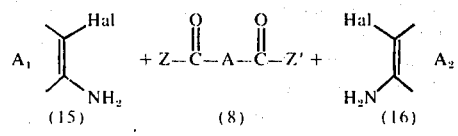

to give the corresponding acid amide of the formula

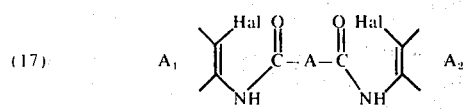

and subsequent cyclisation to the corresponding bis-benzoxazolyl derivative. The cyclisation reaction is carried out in the presence of polar solvents which are chemically inert towards the reactants, further in the presence of hydrogen halide binding agents and copper catalysts. "Hal" in the formulae hereinabove represents chlorine or bromine, and all other substituents have the meanings indicated previously herein.

As examples of polar solvents which are inert towards the reactants there may be mentioned dimethyl formamide, dimethyl sulphoxide, N-methylopyrrolidine, or nitrobenzene. As hydrogen halide binding agents there may be cited: alkali acetate, magnesium oxide, organic bases such as pyridine etc. Examples of copper catalysts are: copper-I-chloride, copper-II-chloride, copper acetate, copper oxides, elementary finely divided copper etc.

This manufacturing process proves particularly advantageous for the manufacture of symmetrical compounds of the formulae (2) to (5).

The new compounds defined above show a more or less pronounced fluorescence in the dissolved or finely divided state. They can be used for the optical brightening of the most diverse synthetic, semi-synthetic or natural organic materials or substances which contain such organic materials.

As examples thereof there may be mentioned the following groups of organic materials, in so far as an optical brightening of these is possible, it being understood that the survey which follows is not intended to express any limitation:

I. Synthetic organic materials or high molecular weight:

a. polymerisation products based on organic compounds containing at least one polymerisable carbon-carbon double bond, that is to say their homopolymers or copolymers as well as their after-treatment products such as, for example, cross-linking, grafting or degradation products, polymer blends, or products obtained by modification of reactive groups, for example polymers based on $\alpha,\beta$-unsaturated carboxylic acids or derivatives of such carboxylic acids, espeically on acrylic compounds (such as, for example, acrylic esters, acrylic acid, acrylonitrile, acrylamides and their derivatives or their methacryl analogues), on olefine hydrocarbons (for example ethylene, propylene, styrenes or dienes and also so-called ABS polymers), and polymers based on vinyl and vinylidene compounds (for example vinyl chloride, vinyl alcohol and vinylidene chloride);

b. polymerisation products which can be obtained by ring opening, for example, polyamides of the polycaprolactam type, and also polymers which are obtained both through polyaddition and through polycondensation, such as polyethers or polyacetals, c. polycondensation products or precondensates based on bifunctional or polyfunctional compounds with condensable groups, their homocondensation and co-condensation products, and after-treatment products, for example polyesters, especially saturated (for example ethylene glycol terephthalic acid polyester) or unsaturated (for example maleic acid-dialcohol polycondensates as well as their crosslinking products with copolymerisable vinyl monomers), unbranched and branched (also including those based on polyhydric alcohols, for example alkyd resins) polyesters, polyamides (for example hexamethylenediamine adipate), maleate resins, melamine resins, their precondensates and analogues, polycarbonates and silicones;

d. polyaddition products such as polyurethanes (crosslinked and non-crosslinked) and epoxide resins.

II. Semi-synthetic organic materials, for example, cellulose esters of varying degrees of esterification (socalled 2½ acetate or triacetate) or cellulose ethers, regenerated cellulose (viscose or cuprammonium cellulose), or their after-treatment products, and casein plastics.

III. Natural organic materials of animal or vegetable origin, for example based on cellulose or proteins, such as cotton, wool, linen, silk, natural lacquer resins, starch and casein.

The organic materials to be optically brightened can be in the most diverse states of processing (raw materials, semi-finished goods or finished goods). On the other hand, they can be in the form of structures of the most diverse shapes, for example predominantly three-dimensional bodies such as sheets, profiles, injection mouldings, various machined articels, chips, granules or foams, and also as predominantly two-dimensional bodies such as films, foils, lacquers, coattings, impregnations and coatins, or as predominantly onedimensional bodies such as filaments, fibres, flocks and wires. The said materials can, on the other hand, also be in an unshaped state, in the most diverse homogeneous or inhomogeneous forms of division, such as, for example, in the form of powders, solutions, emulsions, dispersions, latices, pastes or waxes.

Fibre materials can, for example, be in the form of endless filaments (stretched or unstretched), staple fibres, flocks, hanks, textile filaments yarns, threads, non-wovens, felts, waddings, flocked structures or woven textile fabrics, textile laminates, knitted fabrics and papers, cardboards or paper pulps.

The compounds to be used according to the invention are of importance, inter alia, for the treatment of organic textile materials, especially woven textile fabrics. Where fibres, which can be in the form of staple fibres or endless filaments or in the form of hanks, woven fabrics, knitted fabrics, fleeces, flocked substrates or laminates, are to be optically brightened according to the invention, this is advantageously effected in an aqueous medium, wherein the compounds in question are present in a finely divided form (suspensions, so-called microdispersions, or optionally solutions). If desired, dispersing agents, stabilisers, wetting agents and further auxiliaries can be added during the treatment.

Depending on the type of brightener compound used, it can prove advantageous to carry out the treatment in a neutral or alkaline or acid bath. The treatment is usually carried out at temperatures of 20° to 140°C, for example at the boiling point of the bath or near it (about 90°C). Solutions or emulsions in organic solvents can also be used for the finishing according to the invention of textile substrates, as in practised in the dyeing industry in so-called solvent dyeing (pad-heat fixing application, or exhaustion dyeing processes in dyeing machines).

The new optical brighteners according to the present invention can further be added to, or incorporated in, the materials before or during their shaping. Thus they can for example be added to the compression moulding composition or injection moulding composition during the manufacture of films, sheets (for example working into polyvinyl chloride in a single roller mill) or mouldings.

Where fully synthetic or semi-synthetic organic materials are shaped by spinning processes or via spinning solutions/melts, the optical brighteners can be applied in accordance with the following processes:

addition to the starting substances (for example monomers) or intermediates (for example precondensates or prepolymers), that is to say before or during the polymerisation, polycondensation or polyaddition, sprinkling in powder form on polymer chips or granules for spinning solutions/melts, bath dyeing of polymer chips or granules for spinning solutions/melts, metered addition to spinning melts or spinning solutions, and application to the spun tow before stretching.

The optical brighteners according to the present invention can, for example, also be employed in the following use forms:

a. mixed with dyestuffs (shading) or pigments (coloured pigments or especially, for example, white pigments), or as an additive to dye baths, printing pastes, discharge pastes or reserve pastes, or for the after-treatment of dyeings, prints or discharge prints;

b. mixed with "carriers", wetting agents, plasticisers, swelling agents, anti-oxidants, ultraviolet absorbers, heat stabilisers and chemical bleaching agents (chlorite bleach or bleaching bath additives);

c. mixed with crosslinking agents or finishing agents (for example starch or synthetic finishes), and in combination with the most diverse textile finishing processes, especially synthetic resin finishes (for example creaseproof finishes such as wash-and-wear, permanentpress or non-iron), as well as flameproof finishes, soft handle finishes, antisoiling finishes or anti-static finishes, or antimicrobial finishes;

d. incorporation of the optical brighteners into polymeric carriers (polymerisation, polycondensation or polyaddition products, in a dissolved or dispersed form, for use, for example, in coating agents, impregnating agents or binders (solutions, dispersions and emulsions) for textiles, non-wovens, papers and leather;

e. as additives to master batches;

f. as additives to the most diverse industrial products in order to render these more marketable (for example improving the appearance of soaps, detergents, pigments);

g. in combination with other optically brightening substances;

h. in spinning bath preparations, that is to say as additives to spinning baths such as are used for improving the slip for the further processing of synthetic fibres, or from a special bath before the stretching of the fibre;

i. as scintillators for various purpose of a photographic nature, for example, for electrophotographic reproduction, for the optical brightening of photographic layers, optionally in combination with white pigments, for example $TiO_2$.

If the brightening process is combined with textile treatment methods or finishing methods, the combined treatment can in many cases advantageously be carried out with the aid of appropriate stable preparations which contain the optically brightening compounds in such concnetration that the desired brightening effect is achieved.

In certain cases, the brighteners are made fully effective by an after-treatment. This can, for example, represent a chemical treatment (for example acid treatment), a thermal treatment (for example heat) or a combined chemical/thermal treatment. Thus, for example, the appropriate procedure to fllow in optically brightening a series of fibre substrates, for example of polyester fibres, with the brighteners according to the invention is to impregnate these fibres with the aqueous dispersions (or optionally also solutions) of the brighteners at temperatures below 75°C, for example at room temperature, and to subject them to a dry heat treatment at temperatures above 100°C, it being generally advisable additionally to dry the fibre material beforehand at a moderately elevated temperature, for example at not less than 60°C and up to about 130°C. The heat treatment in the dry state is then advantageously carried out at temperature between 120° and 225°C, for example by heating in a drying chamber, by ironing within the specified temperature range or by treatment with dry, superheated steam. The drying and dry heat treatment can also be carried out in immediate succession or be combined in a single process stage.

The amount of the new optical brighteners to be used according to the invention, based on the material to be optically brightened, can vary within wide limits. It is possible to attain a distinct and durable effect even with very small amounts, in certain cases, for example, amounts of 0.0001 per cent by weight. However, amounts of up to about 0.8 per cent by weight and optionally of up to about 2 per cent by weight can be employed. For most practical purposes, it is preferable to use amounts between 0.0005 and 0.5 per cent by weight.

The new optical brightening agents are also particularly suitable for use as additive for wash liquors or heavy duty and domestic detergents, to which they can be added in various ways. They are appropriately added to wash liquors in the form of their solutions in water or organic solvents or in a finely divided form, as aqueous dispersions. They are advantageously added to domestic or heavy duty detergents in any stage of the manufacturing process of the detergents, for example to the slurry before the washing powder is atomised, or during the preparation of liquid detergent combinations. They can be added either in the form of a solution or dispersion in water or other solvents or, without auxiliaries, as a dry brightening powder. For example, the brightening agents can be mixed, kneaded or ground with the active detergents and, in this form, admixed with the finished powder. However, they can also be sprayed in a dissolved or pre-dispersed form on the finished detergent.

Suitable detergents are the known mixtures of active detergents, for example soap in the form of chips and powders, synthetics, soluble salts of sulphonic acid half esters of higher fatty alcohols, arylsulphonic acids with higher and/or multiple alkyl substituents, sulphocarboxylic acid esters of medium to higher alcohols, fatty acid acylaminoalkyl or acylaminoaryl-glycerinesulphonates and phosphoric acid esters of fatty alcohols. Suitable builders which can be used are, for example, alkali metal polyphosphates and polymetaphosphates, alkali metal pyrophosphates, alkali metal salts of carboxymethylcellulose and other soil rede-position inhibitors, and also alkali metal silicates, alkali metal carbonates, alkali metal borates, alkali metal perborates, nitrilotriacetic acid, ethylenediaminotetraacetic acid, and foam stabilisers such as alkanolamides of higher fatty acids. The detergents can further contain, for example: antistatic agents, skin protection agents which restore fat, such as lanolin, enzymes, anti-microbial agents, perfumes and dyestuffs.

The new optical brighteners have the particular advantage that they are also active in the presence of active chlorine donors such as, for example, hypochlorite, and can be used without significant loss of the effects in wash liquors containing non-ionic washing agents, for example alkylphenol polyglycol ethers.

The compounds according to the invention are added in amounts of 0.0005 to 1% or more, based on the weight of the liquid or pulverulent finished detergent. Washing liquors which contain the indicated amounts of the optical brighteners claimed impart a brilliant appearance in daylight when used to wash textiles of cellulose fibres, polyamide fibres, cellulose fibres with a high quality finish, polyester fibres or wool.

The washing treatment is carried out as follows, for example:

The cited textiles are treated for 1 to 30 minutes at 20° to 100°C in a wash liquor which contains 1 to 10 g/kg of a built-up composite detergent and 0.05 to 1%, based on the weight of the detergent, of the claimed brightening agents. The liquor ratio can be 1:3 to 1:50. After they have been washed the textiles are rinsed and dried in the usual manner. The wash liquor can contain 0.2 g/l of active chlorine (for example as hypochlorite) or 0.1 to 2 g/l of sodium perborate as a bleaching additive.

In the example, parts and percentages are always by weight, unless otherwise stated. Unless indicated to the contrary, melting points and boiling points are uncorrected.

EXAMPLE 1

While stirring and expelling the air with nitrogen, 4.5 g of 9,10-dihydrophenanthrene-2,7-dicarboxylic acid dichloride and 6.1 g of 5-phenyl-2-aminophenol are heated for 5 hours to 120° to 130°C. Then 0.5 g of boric anhydride is added and the batch is heated within 1½ hours to 250°C. Then 20 ml of dibutyl phthalate are added and the temperature is raised to 260°C, in the course of which diethylene glycol dibutyl ether is distilled off together with water. When all the diethylene glycol dibutyl ether has been distilled off the temperature of the brown solution is raised within 10 minutes to 292°C. The solution is then allowed to cool, treated with 50 ml of methanol at 70°C, and cooled to 20°C. The crystallised product is filtered off with suction, washed with 200 ml of methanol and dried in vacuo. The resulting product is recrystallised twice from 100 ml and 90 ml respectively of chlorobenzene with the aid of fuller's earth to give 1.9 g of the compound of the formula

(18) 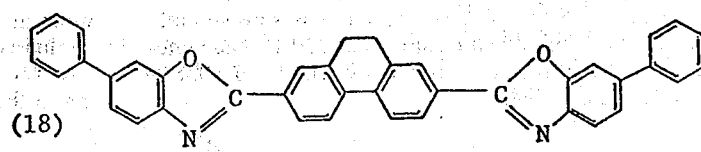

Pale yellow powder; melting point 315°–316°C.

The compound of the formula (6) 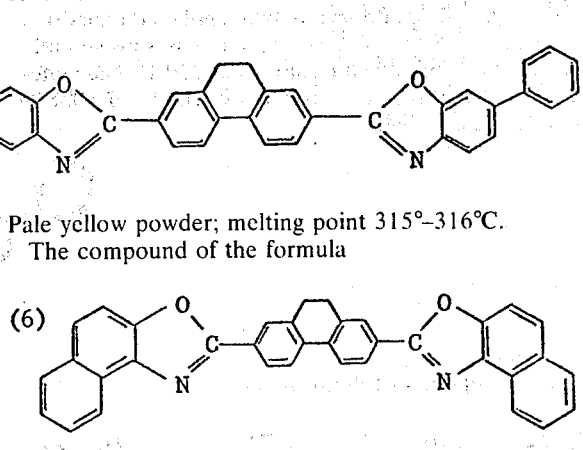

is obtained by using 5.3 g of 1-amino-naphthol instead of 6.1 g of 5-phenyl-2-aminophenol.

9,10-dihydrophenanthrene-2,7-dicarboxylic acid dichloride can be obtained as follows:

While stirring, 12.5 g of 9,10-dihydrophenanthrene-2,7-dicarboxylic acid are heated in 150 ml of toluene together with 30 ml of thionyl chloride and 1 ml of dimethylformamide for 4 hours to 87°–95°C. The yellow solution is concentrated in vacuo to about 50 ml, the concentrate heated under normal pressure to the boil and cooled to 20°C. The crystallised product is filtered off with suction and dried in vacuo to 60°–65°C, yielding 9.4 g of dihydrophenanthrene-2,7-dicarboxylic acid dichloride (m.p. 159°–161°C).

The following compounds are manufactured in similar manner:

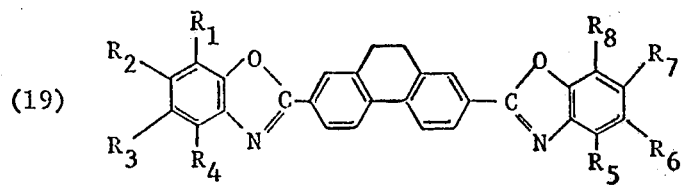

(19)

| Formula | $R_1$ | $R_2$ | $R_3$ | $R_4$ | $R_5$ | $R_6$ | $R_7$ | $R_8$ |
|---|---|---|---|---|---|---|---|---|
| (20) | —H | —CH₃ | —CH₃ | —H | —H | —CH₃ | —CH₃ | —H |
| (21) | —H | —H | —OCH₃ | —H | —H | —OCH₃ | —H | —H |
| (22) | —H | —OCH₃ | —H | —H | —H | —H | —OCH₃ | —H |

EXAMPLE 2

100 parts of terephthalic acid-ethylene glycol polyester are intimately mixed with 0.05 part of the compound of the formula (18) and the mixture is fused at 285°C with stirring. The spinning melt is spun through conventional jets to give strongly whitened polyester fibres with good fastness to light.

EXAMPLE 3

A polyester fabric (e.g. "Dacron" is padded at room temperature with an aqueous dispersion which contains per liter 2 g of the compound of the formula (18) and 1 g of an addition product of about 8 moles of ethylene oxide with 1 mole of p-tert. octylphenol, and then dried at about 70°–80°C. The dry material is subsequently subjected to a brief heat treatment at 220°C. The material treated in this way is strongly whitened and exhibits good fastness to light.

I claim:
1. A compound of the formula

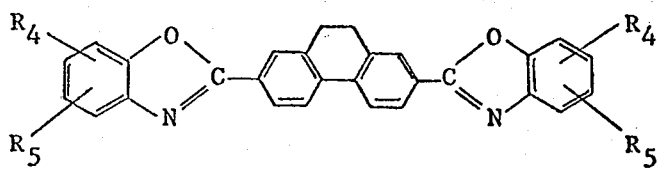

wherein $R_4$ represents alkyl or alkoxy with 1 to 4 carbon atoms, phenyl or phenoxy, $R_5$ represents hydrogen or alkyl with 1 to 4 carbon atoms and $R_4$ and $R_5$ in ortho-position to each other represent tetramethylene, or trimethylene.

2. A compound according to claim 1, corresponding to the formula

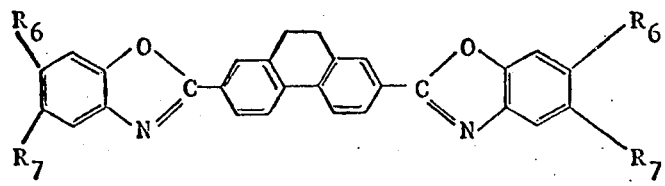

wherein $R_6$ represents alkyl with 1 to 4 carbon atoms, phenyl or phenoxy, and $R_7$ represents hydrogen or alkyl with 1 to 4 carbon atoms, or $R_6$ and $R_7$ together represent tetramethylene or trimethylene.

3. A compound of the formula

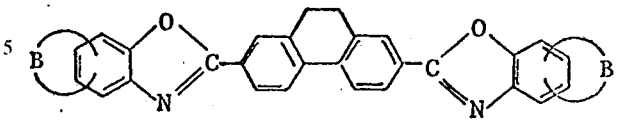

wherein B represents the atoms necessary to form a naphthoxazole ring.

4. The compound according to claim 1, corresponding to the formula

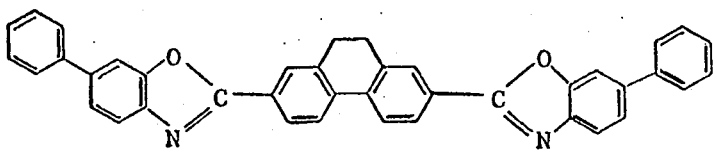

5. The compound according to claim 1, corresponding to the formula

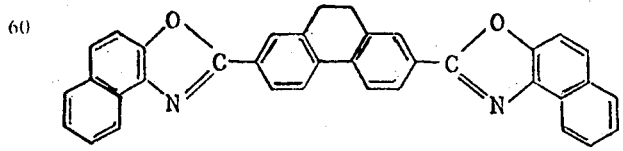

* * * * *